(12) United States Patent
Broglia et al.

(10) Patent No.: US 7,501,398 B2
(45) Date of Patent: Mar. 10, 2009

(54) INHIBITOR OF THE FOLDING OF THE HIV-1-PROTEASE AS ANTIVIRAL AGENT

(75) Inventors: Ricardo Broglia, Milan (IT); Guido Tiana, Milan (IT); Davide Provasi, Gussago (IT)

(73) Assignee: Universita'Degli Studi Di Milano, Milan (IT)

( * ) Notice: Subject to any disclaimer, the term of this patent is extended or adjusted under 35 U.S.C. 154(b) by 148 days.

(21) Appl. No.: 11/186,924

(22) Filed: Jul. 22, 2005

(65) Prior Publication Data

US 2007/0072806 A1 Mar. 29, 2007

(51) Int. Cl.
| | |
|---|---|
| A61K 38/00 | (2006.01) |
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |

(52) U.S. Cl. ........................................ 514/14; 530/328
(58) Field of Classification Search ........................ None
See application file for complete search history.

(56) References Cited

U.S. PATENT DOCUMENTS

2005/0271676 A1* 12/2005 Sette et al. ............... 424/185.1

FOREIGN PATENT DOCUMENTS

WO     WO 01/24810     * 10/2000

OTHER PUBLICATIONS

Abkevich, V.I., et al.; "Specific Nucleus as the Transition State for Protein Folding: Evidence from the Lattice Model"; Biochemistry 1994; Feb. 1, 1994; pp. 10026-10036; vol. 33; American Chemical Society; Cambridge, Massachusetts, U.S.
Baldwin, R. L., et al.; "Is protein folding hierarchic? I. Local structure and peptide folding"; TIBS 24; Jan. 1999; pp. 26-33; Elsevier Science.
Broglia, R.A., et al.; "Folding and aggregation of designed proteins"; Proc. Natl. Acad. Sci. USA Biophysics; Oct. 1998; pp. 12930-12933; vol. 95; The National Academy of Sciences.
Broglia, R.A., et al.; "Resistance proof, folding-inhibitor drugs"; Journal of Chemical Physics; Mar. 8, 2003; pp. 4754-4758; vol. 118, No. 10; American Institute of Physics.
Broglia, R.A., et al.; "Design of HIV-1-PR inhibitors that do not create resistance: Blocking the folding of single monomers"; Protein Science; Jul. 2005; pp. 2668-2681; vol. 14; Cold Spring Harbor Laboratory Press.
Broglia, R.A., et al.; "Reading the Three-Dimensional Structure of Lattice Model-Designed Proteins from Their Amino Acid Sequence"; Proteins: Structure, Function, and Genetics; Jun. 2001; pp. 421-427; vol. 45; Wiley-Liss, Inc.
Broglia, R.A., et al.; "A Folding Inhibitor of the HIV-1 Protease"; Proteins: Structure, Function, and Bioinformatics; Oct. 2005; pp. 928-933; vol. 62; Wiley-Liss, Inc.

Broglia, R.A., et al.; "Hierarchy of events in the folding of model proteins"; Journal of Chemical Physics; Apr. 22, 2001; pp. 7267-7273; vol. 114, No. 16; American Institute of Pnysics.
Go, N; "Theoretical Studies of Protein Folding"; Annual Review of Biophysics and Bioengineering; 1983; pg. 183-210; vol. 12; Annual Reviews Inc.
Ishima, R., et al.; "Folded Monomer of HIV-1 Protease"; The Journal of Biological Chemistry; Dec. 28, 2001; pp. 49110-49116; vol. 276, No. 52; JBC Papers in Press.
Lesk, A., et al.; "Folding units in globular proteins"; Proc. Natl. Acad. Sci. USA Biochemistry; Jul. 1981; pp. 4304-4308; vol. 72, No. 7; The National Academy of Sciences.
Levy, Y., et al.; "The Folding and Dimerization of HIV-1 Protease: Evidence for a Stable Monomer from Simulations"; J. Mol. Biol.; 2004; pp. 67-79; vol. 340; Elsevier Ltd.
Levy, Y., et al.; "Flexibility of Monomeric and Dimeric HIV-1 Protease"; Journal of Physical Chemistry; 2003; pg. 3068-3079; vol. 107; American Chemical Society.
Maity, H., et al.; "Protein folding: The stepwise assembly of foldon units"; PNAS; Mar. 29, 2005; pp. 4741-4746; vol. 102, No. 13; The National Academy of Sciences of the USA.
Panchenko, A., et al.; "Foldons, protein structural modules, and exons"; Proc. Natl. Acad. Sci. USA Biophysics; Mar. 1996, pp. 2008-2013; vol. 93; The National Academy of Sciences.
Ptitsyn, O., et al.; "A Model of Myoglobin Self-Organization"; Biophysical Chemistry 3; 1975; pp. 1-20; North-Holland Publishing Company.
Tiana, G., et al.; "Statistical analysis of native contact formation in the folding of designed model proteins"; Journal of Chemical Physics; Feb. 1, 2001; pp. 2503-2510; vol. 114, No. 5; American Institute of Physics.
Tiana, G., et al.; "Folding and misfolding of designed proteinlike chains with mutations"; Journal of Chemical Physics; Jan 8, 1998; pp. 757-761; vol. 108(2); American Institute of Physics.
Tiana, G., et al.; "Design and Folding of Dimeric Proteins"; Proteins: Structure, Function and Genetics; 2002; pp. 82-94; vol. 49; Wiley-Liss, Inc.
Tomasselli, A., et al.; "Targeting the HIV-protease in AIDS therapy: a current clinical perspective"; Biochimica et Biophysica Acta; 2000; pp. 189-214; vol. 1477; Elsevier Science B.V.
Tomaszek, Jr., T., et al.; "Chromophoric Peptide Substrates for the Spectrophotometric Assay of HIV-1 Protease"; Biochemical and Biophysical Research Communications; Apr. 16, 1990; pp. 274-280; vol. 168, No. 1; Academic Press, Inc.
Xie, D., et al.; "Drug resistance mutations can effect dimer stability of HIV-1 protease at neutral pH"; Protein Science; 1999; pp. 1702-1707; vol. 8; Cambridge University Press.

* cited by examiner

*Primary Examiner*—Cecilia Tsang
*Assistant Examiner*—Marcela M Cordero Garcia
(74) *Attorney, Agent, or Firm*—Shoemaker and Mattare (57) ABSTRACT

The invention relates to the design of inhibitors of the HIV-1-PR homodimer which do not create resistance, by blocking the folding of single monomers with the help of peptides which attach to highly-conserved sites of the monomers.

1 Claim, 8 Drawing Sheets

INHIBITOR OF THE FOLDING OF THE HIV-1-PROTEASE AS ANTIVIRAL AGENT

The present invention relates to a novel class of peptide compounds endowed with inhibitory activity towards HIV-1-protease and, more in particular, it relates to such peptides and their use as antiviral drugs.

BACKGROUND

As human immunodeficiency virus type-1 Protease (HIV-1-PR) is an essential enzyme in the viral life cycle, it is well known in the art that its inhibition can lead to a control of the acquired immune deficiency syndrome (AIDS).

The main properties inhibitory drugs must display are efficiency and specificity. Conventionally, this is achieved by either capping the active site of the enzyme (competitive inhibition) or through the binding to some other parts of the enzyme, hence provoking structural changes which make the enzyme unfit to bind the substrate (allosteric inhibition).

To the extent of our knowledge, all of the known HIV-1-PR inhibitors being available in the market such as, for instance, Indinavir or Sanquinavir, follow the former paradigm.

The great disadvantage in using such compounds in therapy is represented by the drug resistance that may be acquired and that could lead to escape mutants. As a consequence, the above drugs may loose their effectiveness due to the large production of virions in the cell, coupled with the error prone replication mechanism of retroviruses. Under the selective pressure exerted by known drugs, moreover, HIV-1-PR either mutates at the active site or at sites controlling its conformation, in such a way that the enzymatic activity is essentially retained, although the drug is not able to bind to its target anymore. The first signs of the failure of the drug therapy usually takes place 6-8 months after the starting of the treatment. Tomasselli A G and Heinrikson R L, Targetting the HIV-Protease in AIDS therapy: a current clinical perspective. Biochem. Biophys. Acta 2000; 1477: 189-214.

It thus remains of crucial importance to devise novel strategies to block the activity of HIV-1-PR.

Structural conformation, as an example, is a crucial feature in enzyme activities. In order to be active, in fact, the enzymes should stand and remain in, or anyway reach, their proper shape.

Therefore, feasible strategies in finding inhibitors may imply the inhibition of the folding process, known to be responsible of the protein shape, thus somehow preventing the protein to reach a final and active conformation.

A number of experimental and theoretical evidences suggests that globular, single-domain proteins avoid a time-consuming search in conformational space, folding through a hierarchical mechanism. To this extent, Ptitsyn and Rashin observed a hierarchical pathway in the folding of Mb [Ptitsyn O B and Rashin A A model of myoglobin self-organization. Biophys. Chem. 1975; 3: 1-20]. Lesk and Rose identified the units building the folding hierarchy of Mb and RNase on the basis of geometric arguments [Lesk A M and Rose G D. Folding units in globular proteins. Proc. Natl. Acad. Sci. USA 1981; 78: 4304-4308], deriving the complete tree of events which lead these proteins to the native state. Maity and coworkers found, through equilibrium and kinetic hydrogen exchange experiments, that the folding of cytochrome c, composed of five foldon units in the native conformation, proceeds by the stepwise assembly of the foldon units rather than through one amino acid at a time [Maity H, Maity M, Krishna M M G, Mayne L and Englander S W, The stepwise assembly of foldon units, Proc. Natl. Acad. Sci. USA 2005; 102: 4741-4746]. All of these studies describe a framework where small units composed of few consecutive amino acids build larger units which, in turn, build even larger ones, which eventually involve the whole protein [Baldwin R L and Rose G D, Is protein folding hierarchic? TIBS 1990; 24: 26-83]. The kinetic advantage of this mechanism is that, at each level of the hierarchy, only a limited search is needed for the smaller units to coalesce into the larger units belonging to the following level [Panchenko A R, Luthey-Schulten Z and Wolynes P G. Proc. Natl. Acad. Sci. USA 1995; 93: 2008-2013].

Lattice model calculations [Broglia R A and Tiana G., Hierarchy of Events in the folding of model proteins. J. Chem. Phys 2001; 114: 7267-7273; Tiana G and Broglia R A., Statistical Analysis of Native Contact Formation in the Folding of Designed Model Proteins. J. Chem. Phys. 2001; 114 2503-2507] have shown that the folding of a single domain monomeric protein follows, starting from an unfolded conformation, a hierarchical succession of events, namely: 1) formation of few (2-4) local elementary structures (LES, containing 20%-30% of the proteins amino acids) stabilized by few highly conserved, strongly-interacting, "hot" [G. Tiana, R. A. Broglia, H. E. Roman, E. Vigezzi and E. Shakhnovich, Folding and Misfolding of Designed Protein-like Folding and Misfolding of Designed Protein-like Chains with Mutations, J. Chem. Phys 1998, 108: 757] hydrophobic amino acids (≈8% of the proteins amino acids) lying close along the polypeptide chain; 2) docking of the LES into the postcritical folding nucleus [Abkevich V I, Gutin A M and Shakhnovich E I, Specific nucleus as the transition state for protein folding, Biochemistry 1994 33:10026-10031], that is the formation of the minimum set of native contacts which bring the system over the major free energy barrier of the whole folding process; 3) relaxation of the remaining amino acids on the native structure shortly after the formation of the folding nucleus.

The "hot" sites which stabilize the LES are found to be very sensitive to (non-conservative) point mutations. As most of the protein stabilization energy is concentrated in these sites, the mutation of one or two of them has a high probability of denaturing the native state. On the other hand, mutating any other site ("cold" sites, even those "cold" sites belonging to the LES) has in general little effect on the stability of the protein [G. Tiana, R. A. Broglia, H. E. Roman, E. Vigezzi and E. Shakhnovich, Folding and Misfolding of Designed Protein-like Folding and Misfolding of Designed Protein-like Chains with Mutations, J. Chem. Phys 1998, 108: 757; Broglia R A, Tiana G, Pasquali S, Roman H E, Vigezzi E, Folding and Aggregation of Designed Protein Chains, Proc. Natl. Acad. Sci. USA 1998, 95:12930].

Making use of the same model it has been shown that it is possible to destabilize the native conformation of a protein making use of peptides whose sequence is identical to that of the protein LES [Broglia R A, Tiana G and Berera R, Resistance proof, folding-inhibitor drugs, J. Chem. Phys. 2003 118:4754]. Such peptides interact with the protein, in particular with their complementary fragments in the folding nucleus, with the same energy and through the same highly conserved amino acids which stabilize the folding nucleus, thus competing with its formation.

Among the advantages of these folding inhibitors with respect to conventional ones, it is worth pointing out that it is unlikely to observe the protein developing resistance through mutations. In fact, the present inhibitor binds to a LES essentially through the "hot" and "warm" amino acids of these structures, and a protein cannot mutate a LES [G. Tiana, R. A. Broglia, H. E. Roman, E. Vigezzi and E. Shakhnovich, Folding and Misfolding of Designed Protein-like Folding and Misfolding of Designed Protein-like Chains with Mutations, J. Chem. Phys 1998, 108: 757] and, in any case, not those "hot" amino acids which are essential to stabilize it as well as to bind to the other LES so as to form the folding nucleus, under risk of denaturation.

In this respect it is worth noting that neutral mutations (e.g., hydrophobic-hydrophobic) of these hot amino acids are possible, as they do not change in any remarkable way the stability of the corresponding LES, nor the strength and specificity with which LES dock to form the folding nucleus.

SUMMARY OF THE INVENTION

The present invention refers to a novel class of HIV-1 PR inhibitors which effectively interferes with the folding mechanism of the protein itself, thus destabilizing it and making it prone to proteolysis.

As these inhibitors are expected to be highly specific and perdurable efficient, their role as pharmacologically active drugs is of utmost importance.

In fact, as the mutations induced by these drugs will necessarily affect important sites for the folding and, hence, for the stability of the protease, they would consequently lead to the denaturation of the protease itself.

Figure 1:
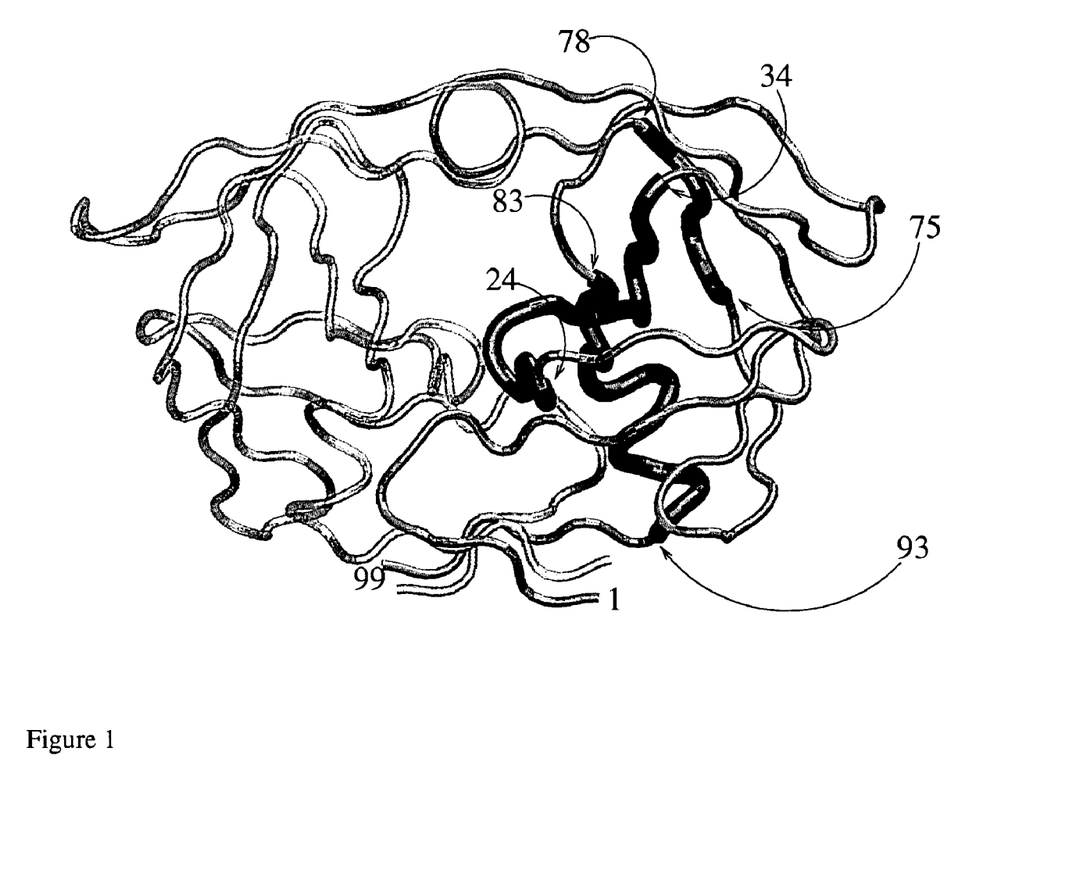
FIG. 1: A cartoon of the native conformation of the HIV-1-PR homodimer. Each monomer contains 99 aa. In the monomer displayed to the right the LES associated with this monomer are evidenced in dark gray.

HIV-1-PR is a homodimer (cf. FIG. 1; PDB code 1BVG), that is a protein whose native conformation is built out of two identical disjoint chains. Sedimentation equilibrium experiments have shown that, in a neutral solution (pH=7, T=4° C.), the protease folds according to a three-state mechanism (2U->2N->$N_2$), consistently populating the monomeric native conformation N. Xie D, Gulnik S, Gustchina E, Yu B, Shao W, Qoronfleh W, Nathan A and Erickson J W. Drug resistance mutations can affect dimer stability of HIV-1 protease ar neutral pH. Protein Science 1999; 8: 1702-1713.

This result is supported by NMR studies of mutants where the interaction across the interface is weakened but the monomer retains its native conformation [Ishima R, Ghirlando R, Todzser J, Gronenborn A M, Torchia D A and Louis J M. Folded monomer of HIV-1 protease. J. Biol. Chem 2001 276: 49110-49116], by all-atom simulations of the HIV-PR monomer in explicit solvent [Levy Y. and Caflisch A. The flexibility of monomeric and dimeric HIV-1 PR. J. Phys. Chem. B 2003 107: 3068-3079] and by Gō-model simulations [Gō N, Int. J. Pept. Prot. Res. 1975; 7:313] of the dimer [Levy Y, Caflisch A, Onuchic J N and Wolynes P G. The folding and dimerization of HIV-1 Protease: evidence for a stable monomer from simulations; J. Mol. Biol. 2004; 340: 67-79].

The dimer dissociation constant (2N->$N_2$) is found to be $k_d$=5.8 μM at T=4° C. [Xie D, Gulnik S, Gustchina E, Yu B, Shao W, Qoronfleh W, Nathan A and Erickson J W, Drug resistance mutations can affect dimer stability of HIV-1 protease ar neutral pH. Protein Science 1999; 8: 1702-1713.] For instance, in a 30 μM solution, 44% of proteins are in the monomeric form. This allows to conclude that, at neutral pH, each monomer of the protein folds following the same hierarchical folding mechanism of single domain, monomeric proteins [Tiana G and Broglia R A. Folding and design of dimeric proteins. Proteins 2002; 82-92]. After the monomer has reached the native state, it diffuses to find another folded monomer to associate with.

Model calculation, evolutionary data, static energy properties, protection factors and j-values, indicate that segments 24-34 ($S_2$), 83-93 ($S_8$) and likely 75-78 ($S_7$) may qualify as LES of the HIV-1-PR monomer and, consequently, as leads of inhibitors of the enzyme [cf. Broglia R A, Tiana G, Sutto L, Provasi D, Simona F, Design of HIV-1-PR inhibitors which do not create resistance: blocking the folding of single monomers, q-bio/002005 (preprint) and refs. therein].

Segment $S_7$ is a so called open LES [R. A. Broglia and G. Tiana, Reading the three-dimensional structure of a protein from its amino acid sequence, Proteins 2001 45:421], being too short to be specific. Concerning the other two LES, $S_2$ is much less structured than $S_8$. In fact, while $S_2$ is stabilized by approximately ten native contacts, double as many contacts contribute to $S_8$. Furthermore, essentially all contacts in $S_2$ are of type I–(i+2), that is next-to-nearest-neighbor contacts, and thus highly local. On the other hand the stability of $S_8$ is uniformly distributed among contacts between amino acids separated by one, two, three and four residues, that is of type i–(i+n) with n=2, 3, 4 and 5. The larger range of these local contacts as compared to those associated with $S_2$ implies a larger collectivity in the transition which brings the segment 83-93 from the denaturated to the native conformation, as compared to that associated with segment 24-34. These facts strongly suggest that p-$S_8$ is likely to be considerably more specific than p-$S_2$, and thus less toxic. These comments do not mean that both $S_2$ and/or $S_7$ cannot be used as effective inhibitors of the HIV-1-PR or as leads to such molecules. It only means that the model calculations and experimental insight indicate $S_8$ as a more promising inhibitor.

From all the above, the segment 83-93 ($S_8$) qualifies to all account as LES of the HIV-1-PR monomer, making the peptide p-$S_8$ (=83N, 84I, 85I, 86G, 87R, 88N, 89L, 90L, 91T, 92Q, 93I) a reliable lead to an efficient, highly selective (little toxic), perdurable (unlikely to generate escape mutants) inhibitor of the folding of the HIV-1-PR monomer and thus of the enzyme itself.

The invention thus relates to a class of inhibitors of the HIV-1-Protease which act by destabilizing the native state of the protein monomers and which are likely not to induce resistance.

It is therefore a first object of the present invention a class of peptides having the following amino acid sequence SEQ ID NO:1 and any modification thereof either obtained by:
(a) adding residues V. PV or TPV at the N-terminal; and/or
(b) adding residues G, GA, or GAT at the C-terminal; and/or
(c) making conservative mutations in any of the above sequences; and/or
(d) making the retro-inverse sequence; and/or
(e) removing one, two or three residues either at the N- or at the C-terminal; and/or
(f) adding at the N- or C-terminal polar and/or charged amino acids in order to improve the solubility of the peptide.

The inhibitors of the present invention are peptides having the same sequence of fragment 83-93 of the wild-type HIV-1 Protease, that is the peptide having the afore-mentioned sequence and any of the variations as per items from (a) to (f).

In the present description, unless otherwise provided, the above amino acid sequence of the peptide object of the invention is conventionally represented through the one-letter code, each defining a single natural amino acid.

By "p-LES" we intend, unless otherwise provided, a short chain of amino acids, of typical size of 10 amino acids or, more generally, of the order of N/10 amino acids, wherein N is the number of amino acids in the target protein.

By "hot" amino acid we intend amino acids which play a central role in the folding of a protein. Non-conservative mutation of these amino acids lead, as a rule, to protein denaturation.

By "LES" (Local Elementary Structure) we intend the first native structures formed very early in the folding process (also conventionally known as foldons or folding domains).

These structures are stabilized by strongly interacting, as a rule hydrophobic, highly conserved ("hot") amino acids.

"Closed LES" are well structured LES sequences and play an important role also in the formation of the post-critical folding nucleus.

"Open LES" are less structured LES; unlike closed LES, it has been observed that they do not display, when isolated in the solvent, any important native contact.

By "post-critical folding nucleus (FN)" we intend the minimum set of native contacts needed to overcome the highest free energy barrier encountered by the protein in the whole folding process. Most, if not all, of these contacts arise from the native contacts internal to each LES and from those resulting from the docking of the LES, an event which is essentially controlled by the closed LES.

By "peptide or peptidic inhibitor" we intend, unless otherwise defined, a peptide displaying a sequence identical to a segment of the target protein which blocks its folding and thus its specific biological function. By "control peptides" we intend short peptides, having typically a sequence of 8 or 12 amino acids, which correspond to the sequences of the target protein other than LES.

As formerly reported, the amino acid sequence of the novel class of peptide inhibitors according to the invention are those represented by peptide SEQ ID NO:1 and any suitable modification thereof, as per the above modifications being coded through items from (a) to (f).

The above substitutions are those conventionally known in the art and may comprise, for instance, the substitution of one or more amino acids with analogue ones. Typical substitutions may thus comprise the replacement of a given hydrophobic amino acid with another hydrophobic amino acid without, of course, substantially changing the inhibitory properties of the given peptide.

Moreover, in order to improve the solubility of such peptide, the addition of polar and/or charged amino acids or, alternatively, the shortening of the chain itself by loosing one or two hydrophobic amino acids at carbon C and/or nitrogen—terminals may be also carried out.

In addition, any mutation through replacement of a hydrophobic amino acid with another less hydrophobic amino acids may also be carried out.

Finally, any modification according to items (c) and (d) comprising conservative mutations and/or retro-inverse sequence are all well known in the art (e.g., a conservative mutation is the substitution of D with E).

The novel peptide inhibitor having sequence SEQ ID NO:1 and as well as any suitable modification thereof may be prepared by well known techniques according to conventional methods of the chemistry of peptides.

Typically, any such inhibitors may be synthesized by properly coupling each of the amino acids forming the peptide, in the proper sequence; alternatively they can be suitably prepared by properly coupling shorter peptide segments so as to finally lead to the desired peptide. In any of the above cases, known preparatory methods may also contemplate solid phase syntheses (see the following experimental section).

As the peptide having sequence SEQ ID NO:1 and any variation thereof, according to the present invention, have been, found as inhibitors of the folding of HIV-1 protease, such peptides can be advantageously employed in therapy, in the treatment of the acquired immune deficiency syndrome (AIDS) or related disorders.

It is therefore a further object of the invention a method for the treatment of the acquired immune deficiency syndrome (AIDS), which method comprises administering to a mammal in need thereof an effective amount of the above peptide inhibitor or any suitable variation thereof, as formerly reported.

Likewise, it is an additional object of the invention a peptide having sequence SEQ ID NO:1 and any suitable variation thereof, as a medicament.

The medicament may be thus employed, when suitably formulated according to known methods, for the treatment of the acquired immune deficiency syndrome (AIDS) and related disorders.

To this extent, however, it is worth pointing out that as the compounds of the invention are peptides, they could be digested by cell enzymes or cause allergies, once administered. Hence, they could be also used as leads for the design of non-peptidic inhibitors void of the above drawbacks or the use of D-amino acids may be contemplated.

Various aspects and embodiments of the present invention are now described by way of examples and figures, also with reference to peptide mimetics and solubility of the inhibitor peptide.

BRIEF DESCRIPTION OF THE DRAWINGS

FIG. 6: The effect of mutations on a number of sites of the monomer of the HIV-1-PR (x-axis) on the stability $p_N$ of the native state of the protein (y-axis), calculated making use of a generalized $C_a$ Go-model [Gō N, Int. J. Pept. Prot. Res. 1975; 7:313; Broglia R A, Tiana G, Sutto L, Provasi D, Simona F, Design of HIV-1-PR inhibitors which do not create resistance: blocking the folding of single monomers, q-bio/002005 (preprint)]. Solid crosses indicate the stability of the native conformation of the monomer alone (at the biological temperature T=2.5 kJ/mol), while the solid dots report the value of $p_N$ of the monomer in presence of three p-LES of type p-$S_8$=83-93. The point drawn at mutation site=0 indicate the results associated with the wild-type sequence. The lines are to guide the eye.

DESCRIPTION OF THE PREFERRED EMBODIMENT(S)

The following examples are herewith intended to better illustrate the present invention without posing any limitation to it.

EXAMPLE 1

Figure 2:
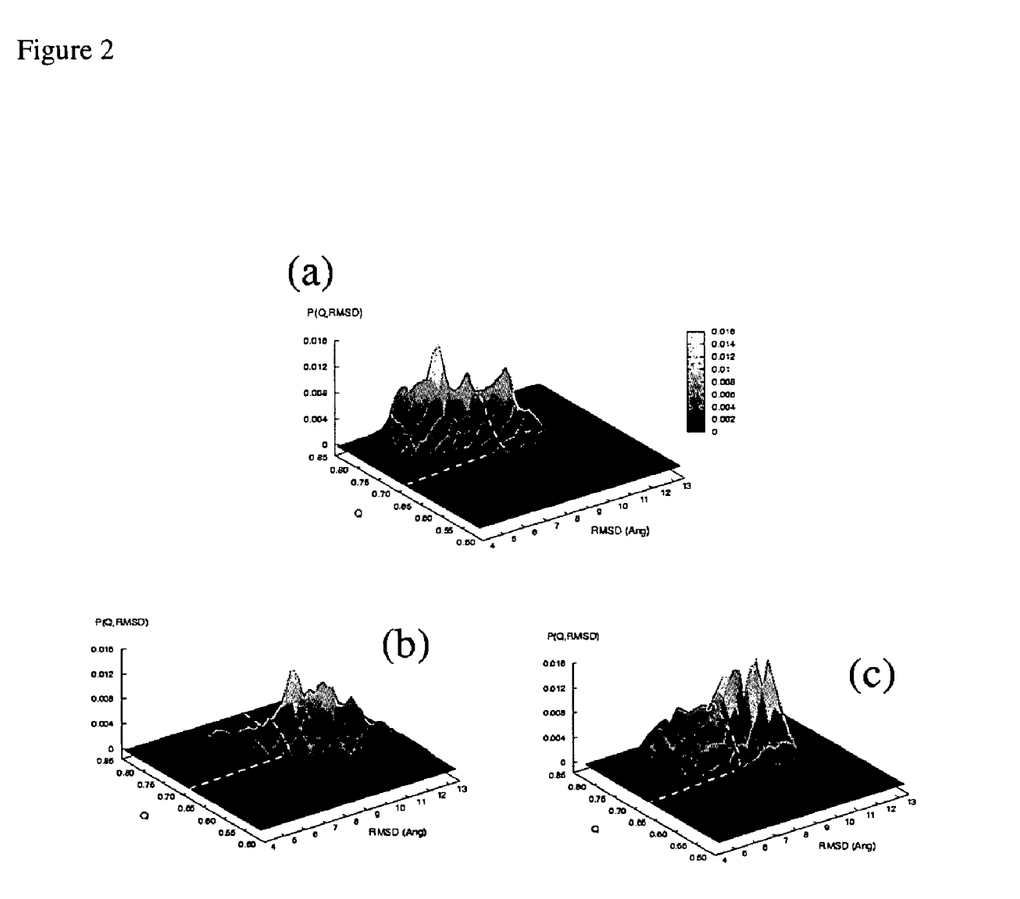
FIG. 2: The equilibrium probability of the HIV-1 PR monomer as a function of the energetic parameter $q_E$ and of the RMSD for the monomer alone (a), the system composed of the monomer and 3 peptides p-$S_8$ (b) and of the monomer and 3 peptides corresponding to the sequence 5-15 control peptide (c). The dashed curve indicates the native state.

Equilibrium simulations [Broglia R A, Tiana G, Sutto L, Provasi D, Simona F, Design of HIV-1-PR inhibitors which do not create resistance: blocking the folding of single monomers, q-bio/002005 (preprint)] of a system composed of the HIV-1-PR monomer and a number of p-S8 have been performed. The joint probability distribution $p(q_E, RMSD)$ of the native relative energy fraction $q_E$ and of the normalized (i.e., the total probability divided by the number of residues) RMSD for the case of 3 p-$S_8$ at T=2.5 kJ/mol are displayed in FIG. 2(*b*), to be compared with that of the monomer alone (FIG. 2(*a*)). The effect of the p-$S_8$ is to decrease drastically the population of the native state and increase at the same time that of the unfolded state.

Figure 3:
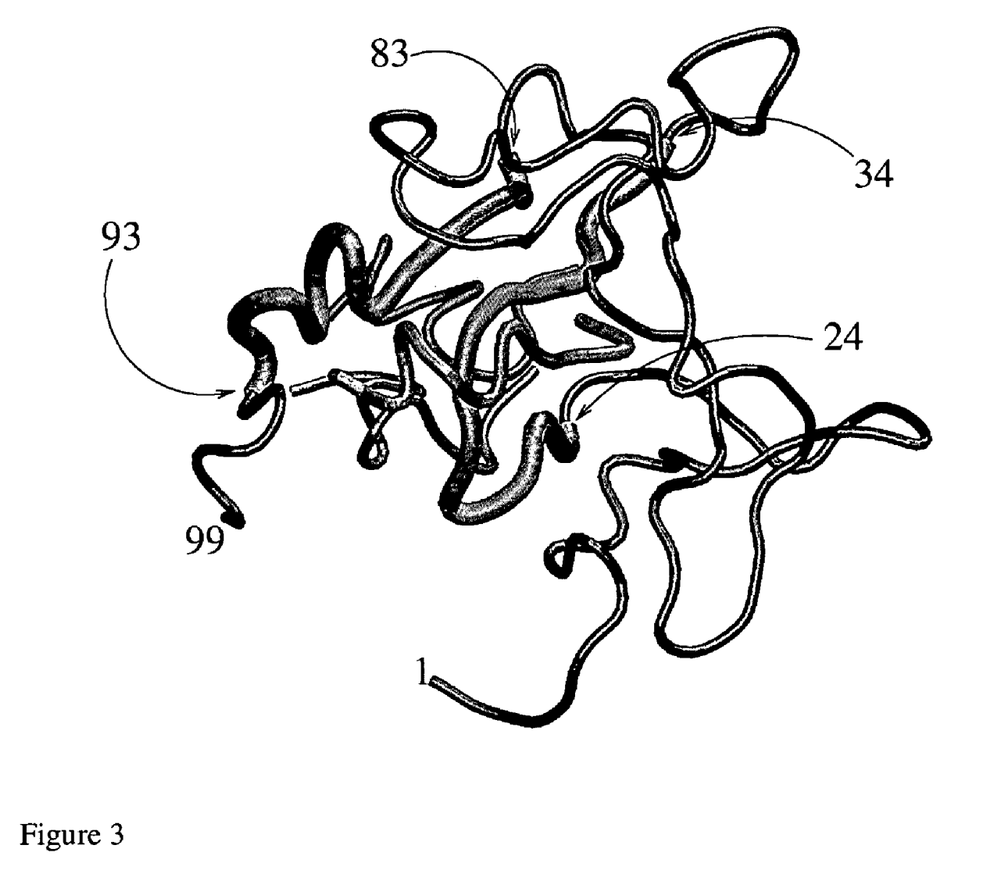
FIG. 3: A snapshot of an unfolded conformation of the HIV-1-PR monomer taken from the simulation associated with the results displayed in FIG. 2, where the (three) peptides p-$S_8$ prevent the folding nucleus to form.

The increase of the peak associated with the unfolded state is caused by the appearance of conformations where the p-$S_8$ peptides are bound to the fragment 24-34 (i.e. the $S_2$-LES) of the protein, preventing the actual $S_8$ LES to find its native conformation. An example of this situation corresponding to the values $q_E$=0.6 and RMSD=11 Å is shown in FIG. 3. The corresponding conformation is particularly stable because the interaction between the peptide p-$S_8$ and the monomer is of the order of −165 kJ/mol, an energy which is of the same order of magnitude to that which stabilizes the folding nucleus of the protein. Note also that more than one p-$S_8$ is able to bind at the same time to the monomer, increasing the degree of denaturation.

Figure 4:
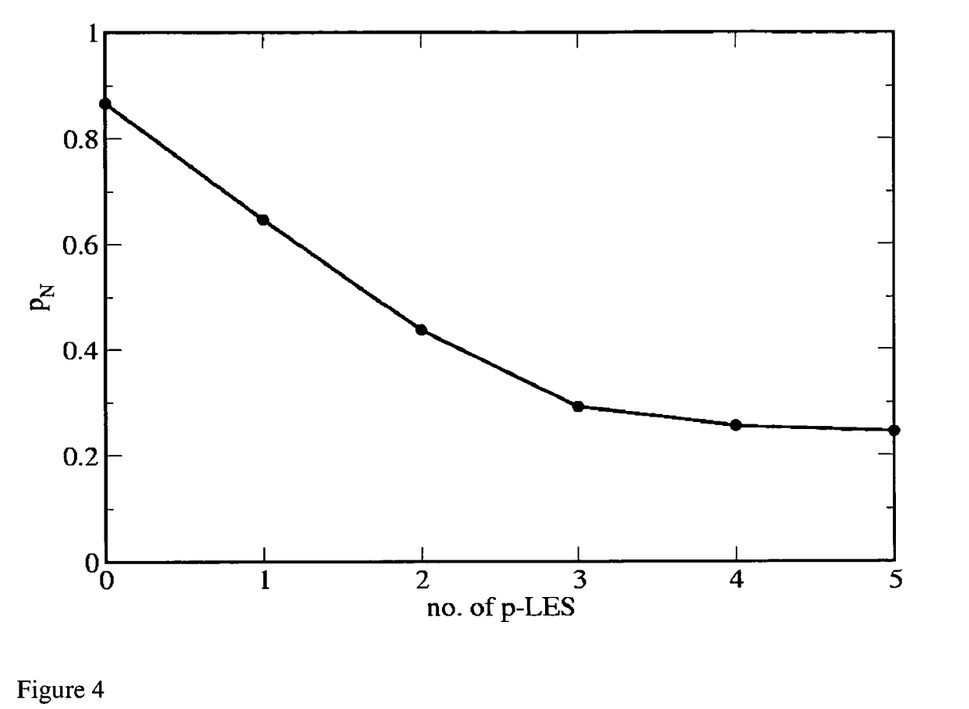
FIG. 4: The equilibrium population of the native state of the monomer as a function of the number of peptides p-$S_8$ (T=2.5 kJ/mol).

In FIG. 4 is displayed the equilibrium population $p_N$ of the native state as a function of the number $n_P$ of p-$S_8$ peptides. The inhibitory effect of the peptides is already present at $n_P$=1 (i.e., a concentration of p-$S_8$ equal to the concentration of protein, in terms of number of chains), in which case the stability of the native state is reduced by >>30% with respect to the situation with no peptides, while for $n_P$=4 the value of $p_N$ becomes >>0.25, as compared with $p_N$=0.83 for the protein by itself. We have repeated the same calculation with control peptides whose sequences are equal to that of the fragments 5-15 and 61-70 of the monomer. While a slight decrease of the stability is observed, control peptides do not disrupt to any extent the folding nucleus of the protein and thus do not prevent the monomer to reach the native state.

The fact that the p-$S_8$ destabilizes the monomeric protease is a sufficient condition to prevent the replication of the virus. This in keeping with the fact that the monomer is at equilibrium with the dimer. Consequently, the destabilization of the monomer shifts the equilibrium of the system towards the unfolded state. Moreover, the fact that the monomeric state is consistently populated under physiological conditions suggests that this shift would be fast and effective.

less, we have also followed the interaction between the p-LES and the HIV-1-PR, starting from the protein in its dimeric native conformation. For this purpose, we have performed $10^{10}$ MCS simulations of a system composed of the dimer and three p-$S_8$ peptides at T=2.5 kJ/mol. The population $p_N$ of the native dimeric state (using the same definition as above) is 0.05, to be compared with 0.304 for the case in which the isolated dimer is evolved starting again from the native conformation.

Figure 5:
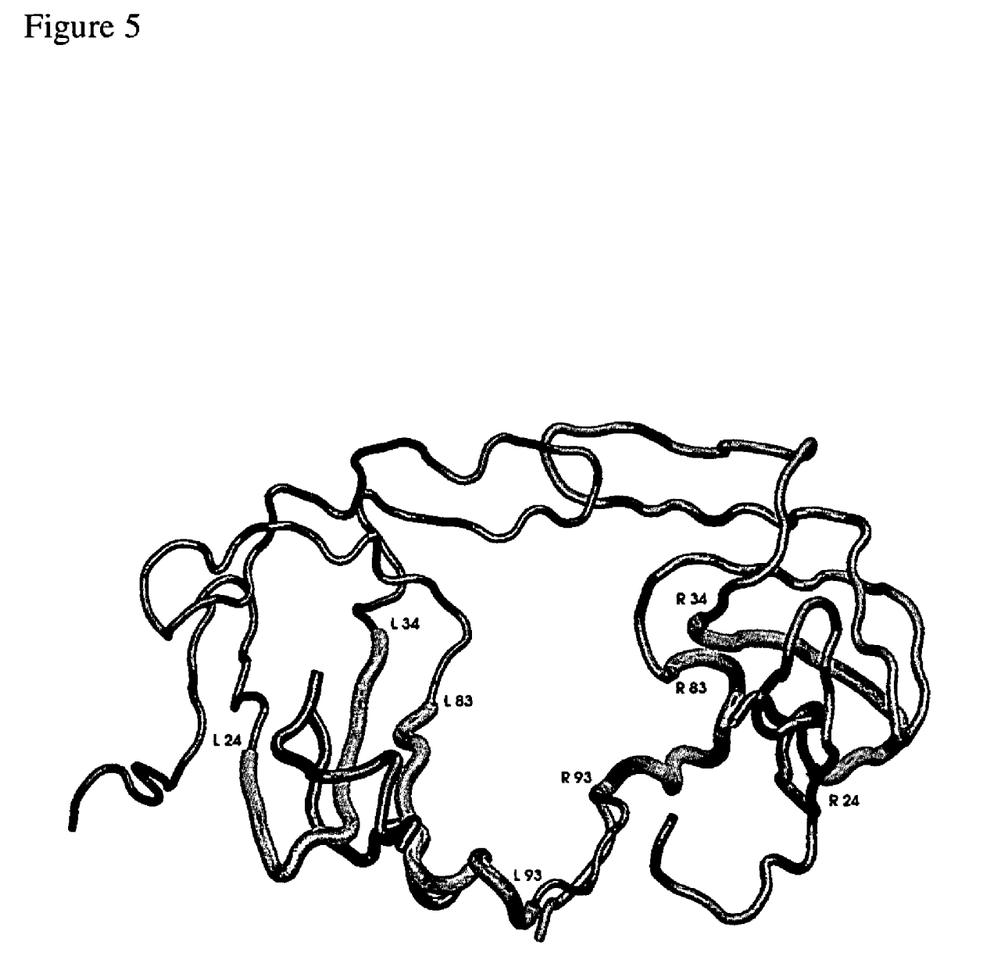
FIG. 5: A snapshot of the simulation of the dimer with 3 p-LES (drawn in black), starting from the native conformation. The LES of the protein are indicated with a thicker gray tube, while the p-LES are highlighted in black. Also given are the number of the initial and final sites of each of the local elementary structures belonging to the left (L) and right (R) drawn monomers.

A snapshot of the result of the three p-$S_8$ plus dimer simulation is shown in FIG. 5. It is seen that the p-$S_8$ peptides are able to bind to the protein, blocking the way of the $S_8$ LES to dock the $S_2$ LES, thus disrupting the folding nucleus. This situation is similar to that shown in FIG. 3 (monomer plus three p-$S_8$ peptides). In the present case, when the p-$S_8$ peptide enters the protein, the RMSD of the associated monomer is increased to a value≈14 Å, which implies that the native conformation is lost.

EXAMPLE 2

In order to assess the effect mutations of the protease have on the effectiveness of the p-$S_8$ as inhibitor, we have performed a number of simulations of mutated protease with and without p-$S_8$. Within the framework of the present model a mutation on a given site is made operative by switching off all the native interactions made by that site in the wild-type sequence, treating them as if they were non-native. We have applied this procedure to a number of sites which are known to be mutated by the virus to escape drugs (e.g., 19, 37, 63, 67, 72 and 95). Also to sites which belong to LES (31, 33 and 85) or which interact with a LES (68).

Figure 6:
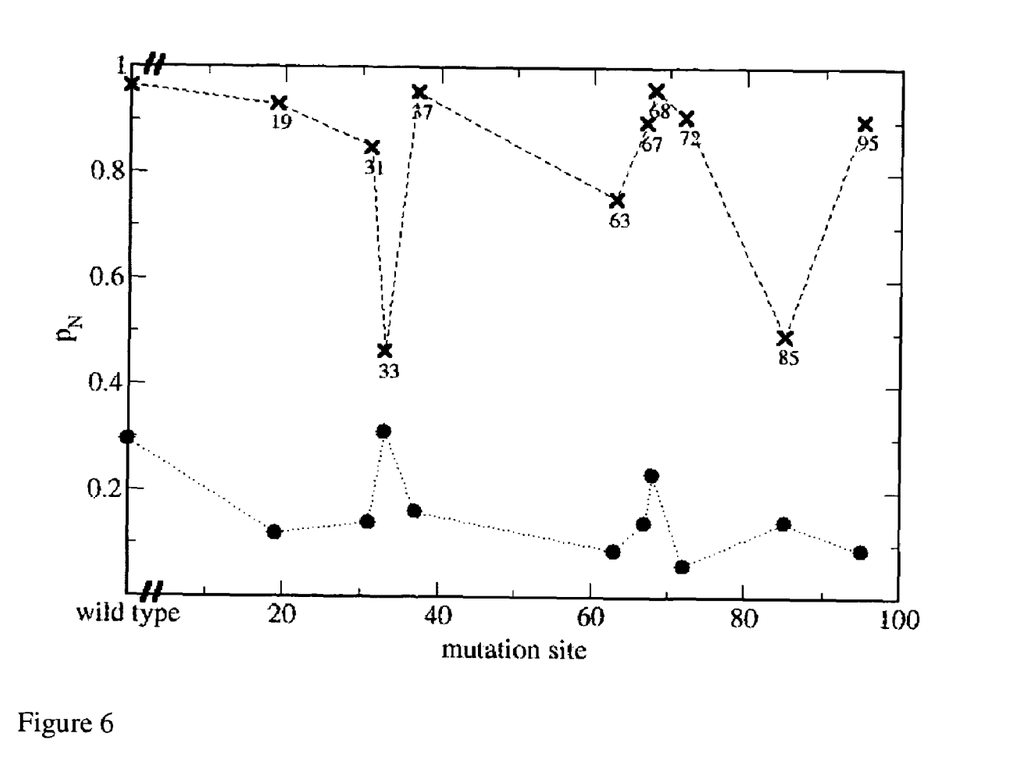

In FIG. 6 we display the population of the native state $p_N$ for the mutated monomeric protease (continuous curve) and for the system composed of the mutated protease and three p-$S_8$ (dotted curve). All mutations except those on sites #85 and 33 have little effect on the stability of the protein. In keeping with this result, the denaturing effect of the p-$S_8$ is fully retained (exception made in the case of mutations on sites #85 and 33), as expected from the fact that the interaction between p-$S_8$ and the monomer is unchanged. In fact, the interaction between p-$S_8$ and the monomer are the same as those which stabilize the monomer itself. Consequently, the mantained stability of the mutated protein is tantamount to the mantained affinity between p-$S_8$ and the mutated protein.

The mutation on site 33 causes a consistent destabilization of the protease, due to the fact that it is a hot site belonging to a LES ($S_2$), site where a large fraction of the stabilization energy of the protein is concentrated. In this case the affinity of the p-$S_8$ to the protease (i.e., to its complementary LES $S_2$) is also diminished and consequently its destabilizing effect is greatly reduced. In any case the net effect of this mutation is that the protein becomes quite unstable.

EXAMPLE 3

Recombinant HIV-1-Protease, expressed in *E. Coli* (Sigma Cat. no. P7338)contained five mutations to restrict autoproteolysis (Q7K, L33I, L36I) and to restrict cysteine thiol oxidation (C67A and C95A). The enzyme was stored at (−70° C. as solution with concentration 25 mg/63 mL in dilute HCl, (pH=1.6)). A chromogenic substrate for HIV-1-PR (Sigma Cat. no. H5535) was obtained as a 1 mg desiccate, diluted with 0.1 ml of DMSO, and stored at −20° C. Protease assisted cleavage between the Nle and the Phe($NO_2$) residues of substrate entails a blue-shift of the absorption maximum (277 nm to 272 nm). It can be adequately monitored observing the continuous decrease of absorbance at 310 nm. A regression of the absorbance at 300 nm against substrate concentration allows to estimate the extinction coefficient of the whole substrate (S=6300±1600 (mol cm)$^{-1}$). Moreover, the absorbance at 300 nm after complete peptidolysis allows to determine a differential extinction coefficient (=1500±250 (mol cm)$^{-1}$) between the whole substrate and the cleaved products. This compares well with a difference of extinction coefficient at 310 nm between the cleaved and the complete substrate of 1200±100 (mol cm)$^{-1}$, reported in Tomaszek T A, Magaard V W, Bryan H G, Moore M L, Meck T D, Chromophoric peptide substrates for the spectrophotometric assay of HIV-1 protease, 1990; Biochem. Biophys. Res. Comm 168:274-280.

Inhibitor peptide (peptide p-S$_8$) from the primary sequence of the HIV-1-PR wild type (PDB code 1BVG) were synthesized by solid phase synthesis (Primm, San Raffaele Biomedical Science Park, Milan) with acetyl and amide as terminal protection group and was estimated to be >95% pure by analytical HPLC after purification. After that 1 mg of inhibitor peptide was dissolved in 100 ml of DMSO, 4 ml of this solution were then diluted with 16 ml of DMSO and 180 ml of the buffer used for assay. The obtained solution (150 mM of peptide p-S$_8$) was used for the experiments.

The buffer was prepared by adding 0.8 mM NaCl, 1 mM EDTA and 1 mM dithiothreitol to a 20 mM phosphate buffer (pH 6).

Other peptides displaying a sequence equal to that of selected fragments of the protease, but not belonging to any LES, as welt as another peptide displaying a random sequence, were also used in the same way as peptide p-S$_8$. The sequences of these control peptides are QILIEICGHK (SEQ ID NO:2) and PLVTIKIGGQL (SEQ ID NO:3) corresponding to fragments 61-70 and 9-19, respectively, of the HIV-1-PR sequence, as well as the LSQETFDLWKLLPEN (SEQ ID NO:4) sequence, which is not related in any way to the protease. We will call these peptides K1, K2 and K3, respectively. To be noted that peptide K2 is rather hydrophobic and only 70% purity could be achieved.

Each measure was performed recording the absorbance at 300 nm (4.13 eV) in a standard UV-vis spectrophotometer (Jasco V-560). The sample had a total volume of 70 µL in Spectrosil Far UV Quartz (170-2700 nm) cuvettes (3.3 mm optical path). The sample in the cuvette was exposed to a constant temperature (37±0.05° C.) provided by continuous circulation of water from a water bath to the cell holder via a circulation pump.

After proper thermal stabilization of the substrate dissolved in the buffer (pH 6), the absorbance at 300 nm was recorded. We performed 6 measures spanning a range of substrate concentrations from 50 µM to 250 µM. The reaction was initiated by adding 2.78 µg of enzyme and recording the absorbance decrease at 300 nm for 1200 sec. In all the reported measures the enzyme has thus a nominal concentration of 1.8 µM. Since, to our knowledge, no accurate measure has been published of the dimerization constant of HIV-1-PR at pH=6.0, it is difficult to estimate precisely the active site concentration in our assay. It should however be noted that the active site concentration only affects the estimation of $k_{cat}$, and has no influence over the enzyme-inhibitor dissociation constants.

The assessment of the enzyme activity in presence of the inhibitor peptides followed a similar routine: the enzyme and the peptide (whose concentration are in a ratio 1:3) were incubated together for approximately 1 min and then added to the substrate. In all the reported measures the final concentration of inhibitor was [I$_0$]=5.4 mM. The Absorbance decrease at 300 nm was recorded for 1200 sec.

Figure 7:
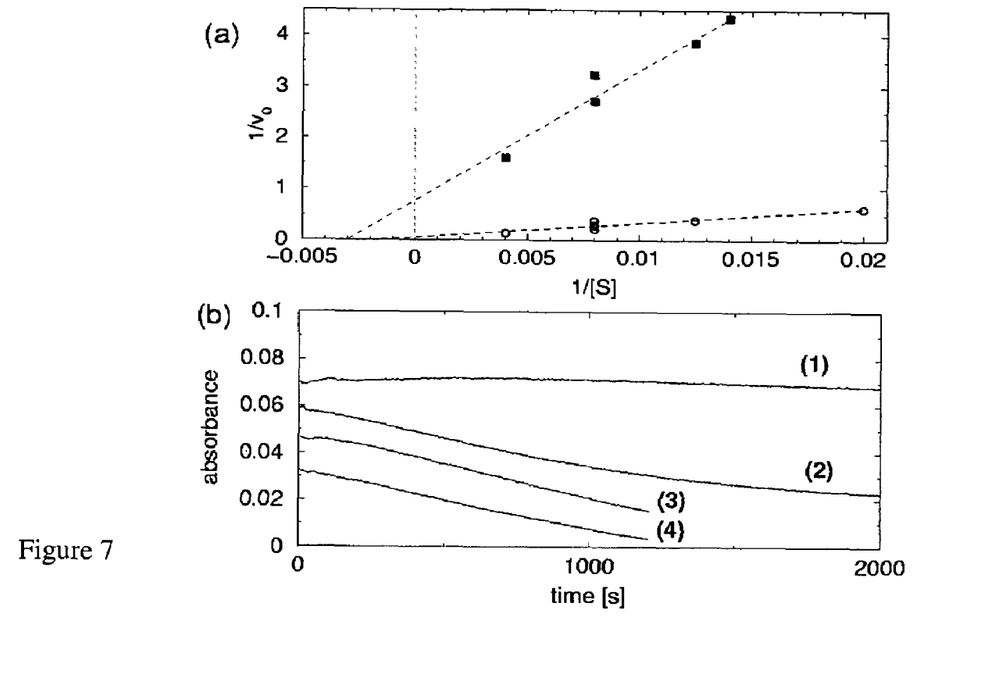
FIG. 7: a) The Lineweaver-Burk plot associated with the protease (empty circles) and the protease complexed with the inhibitor p-$S_8$ (filled squares). The dashed lines are the linear fits to the experimental points. The initial velocities $v_0$ are expressed in terms of absorbance/s, while the substrate concentration [S] is in mM. b) The enzymatic kinetics of the inhibited protease (1), of the protease alone (2), of the protease together with control peptides K1 (3) and K2 (4), measured as change in absorbance of the chromogenic substrate as a function of time. All the curves have been measured at [$S_0$]=125 mM, and have been shifted along the y-axis in order to be easily inspected.

In order to provide a quantitative measure of the enzymatic activity of HIV-1-PR and the inhibitory mechanism of the designed peptides, we have performed a Michaelis-Menten analysis of the data reported in FIG. 7(b), measuring the initial reaction velocity v$_0$ at different substrate concentrations (cf. FIG. 7(a)) [R. A. Broglia, G. Tiana, D. Provasi, F. Simona, L. Sutto, F. Vasile and M. Zanotti, Design of a folding inhibitor of the HIV-1 Protease, to be published, q-bio/0408013]. We obtain an estimate of the dissociation constant K$_M$ for the uninhibited-enzyme/substrate complex (curve (2) of FIG. 7(b)) of 670±860 mM. The maximum velocity of the reaction v$_{max}$ results 0.40±0.52 mM/s, corresponding to a catalytic rate k$_{cat}$=0.25±0.28 s$^{-1}$. Note that the order of magnitude of these results compares well with those reported for the same substrate in ref., that is K$_M$=280±100 mM and k$_{cat}$=7.3 mM/s. The apparent dissociation constant K'$_M$ of the inhibited reaction is 332±191 mM, the maximum velocity being v$_{max}$=0.026±0.011 mM/s (cf. curve (1) of FIG. 7(b)). The fact that the value v$_{max}$ changes in presence of the inhibitor while that of K'$_M$ remains within the experimental error of K$_M$ suggests that the inhibition is compatible with a non-competitive scenario, in which the inhibitor can bind to the free enzyme with a dissociation constant K$_I$ or to the substrate-enzyme complex with a dissociation constant K'$_I$ not significantly different from K$_I$. The results shown in FIG. 7(a) lead in fact to the values K$_I$=380±810 nM and K'$_I$=180±234 nM.

We have repeated similar measures using this time the control peptides K1, K2 and K3 instead of peptide p-S$_8$, and found no appreciable variation in the kinetic parameters with respect to the uninhibited case (cf. curve (3) and (4) of FIG. 7(b)). In the presence of peptide K1 or K2 the reaction displayed initial velocities v$_0$=0.051 µM/s and v$_0$=0.049 µM/s, respectively, essentially identical to the value of v$_0$ obtained from the global fit to the curve (2) of FIG. 7(b).

Ultraviolet CD spectra were recorded on a Jasco J-810 spectropolarimeter in nitrogen atmosphere at room temperature using 0.1 cm path-length quartz cell. Each spectrum was recorded between 260-200 nm. The data were collected at a rate of 10 nm/min with a wavelength step of 0.2 nm and a time constant of 2 s. The spectra were corrected with respect to the baseline and normalized to the aminoacidic concentration. The protein and the peptide were dissolved in a 20 mM phosphate buffer with 0.8 M NaCl at the same concentration used for the activity assays. The CD spectra were analyzed in terms of contribution of secondary structure elements using the K2D method based on comparison with CD spectra of proteins and peptides with known secondary structure.

Figure 8:
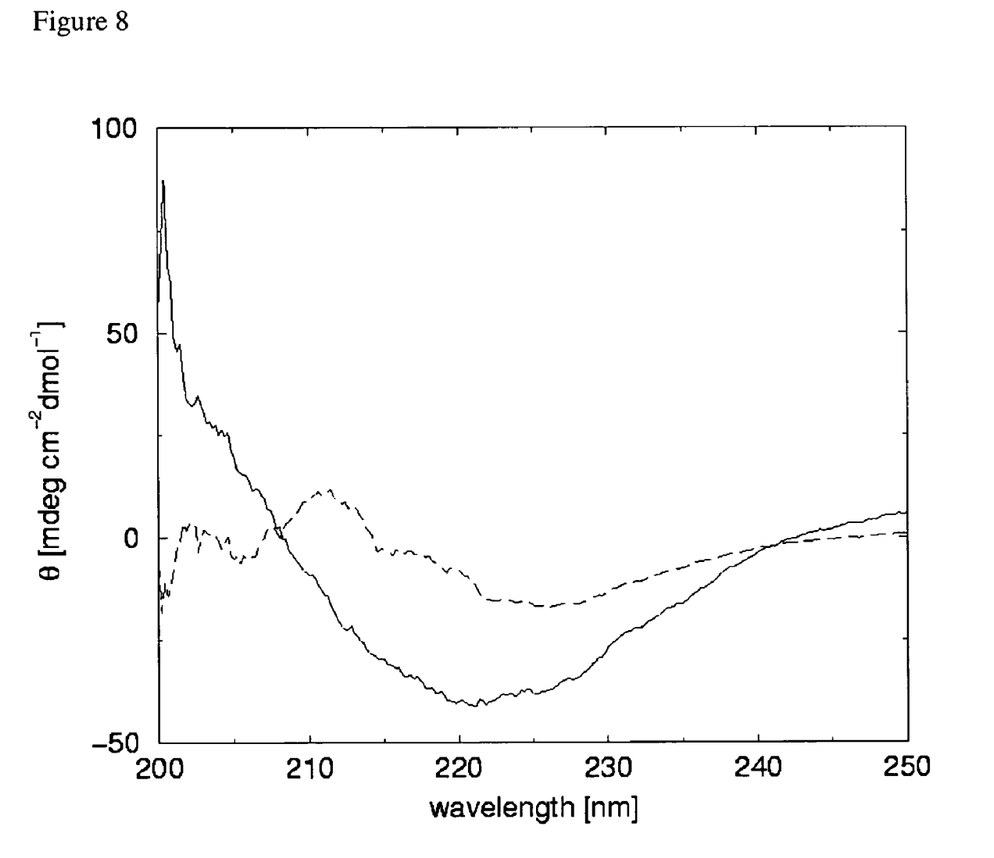
FIG. 8: The circular dichroism spectrum of the protease (solid curve) and of the solution composed of the protease and p-$S_8$ peptide (dashed curve) in the ratio 1:3.

The conformational properties of the inhibited protease have been investigated by means of UV circular dichroism experiments. The CD spectrum of the protease (cf. FIG. 8) under the same conditions used for the activity assay indicate a beta-sheet content of 79%, consistent with the beta character of the native conformation. The CD spectrum of the solution of protease plus p-S$_8$ inhibitor, at the same concentrations and under the same conditions as those of the activity assay, shows a loss of beta-structure (to a beta-sheet content value of 45%), indicating that the protein is, to a large extent, in a non-folded conformation. These numbers compare well with those predicted by the model calculations.

The invention claimed is:

1. A peptide consisting of the amino acid sequence obtained by removing one residue either at the nitrogen N- or at the carbon C-terminal of SEQ ID NO:1 and retroinverse sequences thereof.

* * * * *

SEQUENCE LISTING

<160> NUMBER OF SEQ ID NOS: 4

<210> SEQ ID NO 1
<211> LENGTH: 11
<212> TYPE: PRT
<213> ORGANISM: Artificial Sequence
<220> FEATURE:
<223> OTHER INFORMATION: Designed Peptide

<400> SEQUENCE: 1

Asn Ile Ile Gly Arg Asn Leu Leu Thr Gln Ile
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Fragment 61-70 of the HIV-1-PR sequence

<400> SEQUENCE: 2

Gln Ile Leu Ile Glu Ile Cys Gly His Lys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Fragment 9-19 of the HIV-1-PR sequence

<400> SEQUENCE: 3

Pro Leu Val Thr Ile Lys Ile Gly Gly Gln Leu
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Designed Peptide

<400> SEQUENCE: 4

Leu Ser Gln Glu Thr Phe Asp Leu Trp Lys Leu Leu Pro Glu Asn
1               5                   10                  15